(12) United States Patent
Matkevich

(10) Patent No.: US 12,246,035 B2
(45) Date of Patent: Mar. 11, 2025

(54) ACID-MINERAL COMPOSITION FOR AN ENTERAL SOLUTION

(71) Applicant: Viktor Anatolievich Matkevich, Moscow (RU)

(72) Inventor: Viktor Anatolievich Matkevich, Moscow (RU)

( * ) Notice: Subject to any disclaimer, the term of this patent is extended or adjusted under 35 U.S.C. 154(b) by 678 days.

(21) Appl. No.: 17/419,856

(22) PCT Filed: Dec. 27, 2019

(86) PCT No.: PCT/RU2019/001036
§ 371 (c)(1),
(2) Date: Jun. 30, 2021

(87) PCT Pub. No.: WO2020/162788
PCT Pub. Date: Aug. 13, 2020

(65) Prior Publication Data
US 2022/0072033 A1    Mar. 10, 2022

(30) Foreign Application Priority Data
Feb. 4, 2019    (RU) .................................. 2019103048

(51) Int. Cl.
| | | |
|---|---|---|
| *A61K 33/14* | (2006.01) | |
| *A61K 9/00* | (2006.01) | |
| *A61K 9/08* | (2006.01) | |
| *A61K 31/19* | (2006.01) | |
| *A61K 33/04* | (2006.01) | |
| *A61K 33/42* | (2006.01) | |

(52) U.S. Cl.
CPC ............ *A61K 33/14* (2013.01); *A61K 9/0095* (2013.01); *A61K 9/08* (2013.01); *A61K 31/19* (2013.01); *A61K 33/04* (2013.01); *A61K 33/42* (2013.01)

(58) Field of Classification Search
None
See application file for complete search history.

(56) References Cited

FOREIGN PATENT DOCUMENTS

| | | | | |
|---|---|---|---|---|
| RU | 02178696 | * | 1/2002 | |
| WO | WO-9115467 A | * | 10/1991 | ....... A61K 47/48076 |

* cited by examiner

*Primary Examiner* — Melissa S Mercier
(74) *Attorney, Agent, or Firm* — Nadya Reingand

(57) ABSTRACT

The invention is used in conducting intestinal lavage and enteral correction of body homeostasis disorders, shortening a regeneration period of the mucosa of the gastrointestinal tract (GIT), reducing a rate of extraintestinal complications related to hyperpermeability of the intestinal barrier, and preventing edemas after intestinal lavage at various diseases. The invention includes an acid-mineral composition (AMC) and a solution of sodium phosphate mono-, or twice-, or triple-substituted, or potassium phosphate mono- or twice-substituted, sodium chloride, sodium acetate, potassium chloride, calcium chloride, magnesium sulphate, citric acid, and water. The osmolarity of the solution is preferably in the range from 280 to 310 mOsm/L. The invention may further comprise aminopolycarboxylic acids and short-chain carboxylic (fatty) acids to provide a solution pH from 4.61 to 5.8.

3 Claims, 3 Drawing Sheets

Patient D, aged 44, intoxication by acetic essence, dated 18.01.17

Patient D, aged 44, intoxication by acetic essence, dated 23.01.17

Patient D, aged 44, intoxication by acetic essence, dated 23.01.17

Patient D, aged 44, intoxication by acetic essence, dated 23.01.17

Patient D, aged 44, intoxication by acetic essence, dated 23.01.17

ACID-MINERAL COMPOSITION FOR AN ENTERAL SOLUTION

FIELD OF THE INVENTION

The invention relates to the field of medicine, namely, to gastroenterology, coloproctology, surgery, therapy, allergology, toxicology, narcology, resuscitation science, dermatology, nephrology, combustiology, restorative medicine, etc. and may be used for the purposes of conducting intestinal lavage and enteral correction of body homeostasis disorders, shortening a regeneration period of the mucosa of the gastrointestinal tract (GIT) in a case of its damage or inflammation, reducing a rate of extraintestinal complications related to hyperpermeability of the intestinal barrier, preventing edemas after intestinal lavage at various diseases.

DESCRIPTION OF PRIOR ART

Various acid-mineral compositions used for lavage of the gastrointestinal tract are known in the art. In particular, polyethylene glycol-electrolyte solutions (sold under the Fortrans and Lavacole trade names) are known. These solutions are used for conducting intestinal lavage (IL) for the purpose of detoxifying an organism in cases of acute intoxications [Tenenbein M. Position Statement: Whole Bowel Irrigation/Clinical Toxicology, 1997.—No. 35 (7).—P. 753-762.], preparing the large intestine for diagnostic and surgical interventions [Kostenko N. V. Intestinal Lavage as a Method for Preparing the Large Intestine for an Examination and Operations. Author's abstract of the thesis for PhD in medical sciences, M., 1998.—20 pp.; Delmotte J. S. et al., Ann. Gastroenterology. Hepatol., 1988, 24, n 4 211-216.]. The mechanism of its action is based on the capability to provoke hyperosmolar diarrhea. Macrogol (e.g. Macrogol 4000) included into the solution is an osmotically active substance which molecules are capable of attracting water, including attracting water from the blood circulatory channel into the GIT cavity, thus creating an excessive volume in the intestine and, as a consequence, contractions of its muscle fibers provoking diarrhea.

A disadvantage of this solution is its hyperosmolarity in relation to the plasma, which causes uncontrolled transport of water from the blood circulatory channel into the GIT cavity and due to which blood clotting, a central hemodynamics and microcirculation disorder may develop. Another disadvantage of this solution is that it contains an incomplete set of microelements; therefore, as a result of diarrhea, an organism loses macroelements absent from the solution, which may negatively affect the health condition of a patient. Also, a disadvantage of this solution is that its pH values range from 7.9 to 8.5, causing a shift of the intestine internal medium, which is weak-acid normally, toward the base side, thus creating unfavorable conditions for existence of the normal intestinal flora, i.e. bifido- and lactobacteria for which a weak-acid medium is favorable. A base medium suppresses rises in the normoflora, which are manifested as lowering of their number and facilitates rises in conditionally pathogenic and pathogenic microorganisms, i.e. a basic solution provokes dysbacteriosis of the bowels [Shenderov B. A. Medical Microbial Ecology and Functional Nutrition: in 3 volumes/Shenderov B. A.,—M.: GRANT, 1998.—V. I: Microflora of a Human Being and Animals and Its Functions.—288 P.].

A medication for intestinal lavage is known from Patent RU 2473330, which is an electrolyte solution comprising, as the main active substance, sorbitol in an amount of 60-63 g. Sorbitol relates to the class of hexatomic alcohols and exhibits osmotic activity, owing to which it causes an aperient action on the bowels.

A disadvantage of this solution is that it provokes, similarly to Macrogol, hyperosmolar diarrhea with all the consequences described above. Unlike Macrogol, the use of sorbitol further causes weakness, nausea, vomiting, dizziness, meteorism, hyperglycemia (in patients with decompensated diabetes mellitus), the irritable bowel syndrome and worse absorption of fructose, acidosis, urinary retention, dryness in the mouth and thirst, dehydration, pulmonary congestion, hypotension, tachycardia, pains similar to stenocardia pains, blurred vision, convulsions, rhinitis, chill, pain in the back, allergic reactions including nettle rush. Sorbitol, as contained in the cells of the nerves and the eyes, may become the cause of neuropathy as well as diabetic retinopathy. Big amounts of sorbitol may change the cardiopulmonary function and the renal function. Contraindications to the use of sorbitol are: hypersensitivity, fructose intolerance, decompensated diabetes mellitus, ascites, colitis, cholelithiasis, the irritable large intestine syndrome, obesity. It is not recommended for prolonged use as a laxative [Sorbitol. Description of the substance//Access to: http://www.nebol-eem.net/sorbit.php; http://gipocrat.ru/farmacied_d1_22.phtml].

Thus, a solution comprising sorbitol, if used for conducting intestinal lavage, is capable of provoking clinically significant reactions and is possible only as a laxative used for a short time with due regard to contraindications and the risk of side reactions.

It is known from literary sources that all solutions which physical and chemical properties differ from the physical and chemical characteristics of chyme, negatively affect the blood composition and the condition of the intestine microbiocenosis when the GIT is irrigated [Galperin Yu. M. Digestion and Homeostasis/Galperin Yu. M., Lazarev P. I.,—M.: Nauka, 1986.—304 P.]. When a volume of an irrigating solution of Fortrans type is small (for example, up to 1.5-2 L), these disorders may remain unnoticed owing to compensatory capabilities of the organism. The problem is that for effective cleansing of the GIT and detoxification of an organism a volume of an irrigating solution greater than the GIT volume is required. It amounts, on the average, to 3 liters for an adult patient having a body weight of 60-70 kg. The greater is a volume of an irrigating solution, the more efficient is cleansing of the bowels. Thus, for example, the rule of irrigating the stomach and the large intestine "until irrigating water is clean" exists in the clinical toxicology practice. For this, tens of liters of water are required. At acute intoxications, IL with the use of tens liters of a solution is conducted [Matkevich V. A. Intestinal Lavage at Acute Oral Intoxications/Matkevich V. A., Luzhnikov Ye. A.//Urgent Clinical Toxicology: Manual for Physicians/ed. by Ye. A. Luzhnikov.—M.: Medpractica-M, 2007.—Ch. VI.—pp. 269-276.].

It is known that a composition of the small intestine inner medium (chyme) is rather strictly stabilized [Baklykova N. M., Compositions and Preparation of Media for Intraintestinal Introduction at Peritonitis. —Methodical Recommendations. M., 1986.—19 P.; Galperin Yu. M., Popova T. S., In the book: Methods for Correcting Metabolic Disorders in Urgent and Planned Surgery.—M., 1976.]. The chyme homeostasis is ensured by the bowel microflora and intensive mass exchange between the enteral medium and the blood plasma. These conditions should be taken into account while selecting a solution for irrigating of the bowels. If the physical and chemical characteristics of a solution and chyme are not matched, then, when volumes of the solution are great, the composition of the intestine inner medium is changed, and a physiological gradient of chemical substance concentrations in the bowel cavity and in the blood is changed, which causes their redistribution in the result of which water-electrolytic disorders of the blood plasma appear. A nature and degree of such disorders directly depend on a volume, nature and degree of unbalance of a solution used for irrigation. Thus, for example, if potassium ions are absent from or are insufficient in an irrigating solution, then they move from a medium with a higher concentration, i.e. from the blood plasma, to a medium with a lower concentration, i.e. into the GIT cavity, and are removed together with the solution from the organism. After this, a potassium concentration in the blood plasma is lowered. Potassium loss may be dangerous for health and life of a patient. If a potassium concentration in an irrigating solution is excessive, then an opposite condition appears in the irrigating solution. Mass exchange of other macroelements through the intestine wall follows the same pattern.

A change in concentration values of the blood plasma electrolytes (especially, sodium) entails changes in plasma osmolality and pH, in an organism water balance.

For this reason, the use of solutions, which are non-physiological in relation to chyme, for irrigating the small intestine in a volume greater than 3 L, for example Fortrans, Lavacole or those comprising other osmotically active substances (sorbitol, mannitol, lactulose, etc.), inevitably results in the above-mentioned disorders and negatively affects patients' condition [Baklykova N. M. Possibilities of Using Intestinal Dialysis for Correcting Metabolic Disorders at Acute Surgical Diseases of the Abdominal Cavity Organs// Works of Scientific Research Institute for Emergency Medicine named after N. V. Sklifosovsky. Volume XXIII Moscow. 1976. p. 152.; Glozman O. S., Kasatkina A. P. Modern Methods of Active Therapy of Acute Toxicoses.—M., Medgiz. 1959. 276 P.].

An enteral salt solution (ESS) is known in the art, which was created in accordance with the qualitative composition of anions and cations contained in chyme [Baklykova N. M. Compositions and Preparation of Media for Intraintestinal Introduction at Peritonitis. Methodical Recommendations. M., 1986.—19 P.]. This enteral solution is prepared ex tempore according to a formulation having six variants by dissolving salts with distilled water. According to the author, irrespective of a formulation variant, the ionic composition of a final solution is identical in every case. The composition of this solution, according to the six formulation variants, comprises salts, such as sodium and potassium chloride and phosphate, sodium acetate, calcium chloride and magnesium sulphate, citric acid as well as distilled water as the salt dissolving agent. The solution osmolarity is app. 235 mOsm/L, its pH value ranges from 5.5 to 5.8.

An ESS is used as enteral nourishment at peritonitis as well as for conducting IL at functional intestinal obstructions and acute oral intoxications.

A disadvantage of an ESS is that it may not be stored for a long time, since it becomes turbid in several hours after preparation, and then a sediment is formed in it. For the purpose of preventing the patient's body from heat loss during an IL procedure a solution should be heated up to 37-40° C. before use. Moreover, the solution should be heated up under certain conditions and rules (at a water bath or in a special apparatus). Quick heating or excess heating, even slightly over 40° C., also leads to turbidity. Turbidity of the solution and sedimentation are conditioned by the fact that cations of calcium ($Ca^{2+}$) and magnesium ($Mg^{2+}$), as present in the solution composition, enter into a chemical reaction with anions $SO4^{2-}$ and $PO4^{3-}$, forming insoluble salts $CaSO_4$, $Ca_3(PO_4)_2$ and $MgHPO_4$. It is not permissible to use a turbid solution or a solution containing a sediment, since in such a case its ionic composition does not correspond to the initial composition, and may result in disorders of the blood electrolyte balance during an IL procedure. Instability of the solution composition deteriorates its consumer quality as a commodity.

Another disadvantage of this solution is that organism hyperhydration (edemas) develops rather frequently after an IL procedure [Matkevich V. A. Intestinal Lavage at Acute Oral Intoxications.—Author's abstract of the thesis for PhD in medical sciences, M., 1988]. This disadvantage is associated with the fact that the value of the solution osmotic pressure (235 mOsm/L) is significantly lower than that of the human blood plasma (normal values vary in the range of 280-310 mOsm/kg and are, on the average, 294.1±1.3 mOsm/kg) [Fabian M. J., Proctor K. G. Hemodynamic Actions of Acute Ethanol after Resuscitation from Traumatic Brain Injury. J. Trauma. 2002; 53:864-75]. It is known that a volume and a rate of absorption of a liquid into the GIT directly depend on an osmotic pressure gradient of this liquid and the blood plasma. Due to the fact that the ESS osmotic pressure is lower than a colloid-osmotic pressure of the blood plasma, the solution is easily absorbed from the GIT into the blood. Its arrival in an excess amount leads to formation of edemas deteriorating the patient's condition and requiring special medicinal measures.

Yet another disadvantage of the solution is that the author recommends to use distilled water for preparing it as a salt dissolving agent, no other variants are proposed, which limits technological possibilities of this solution.

Also, an ESS according to Patent RU 2178696 is known, which possesses the disadvantages revealed in the description of the foregoing analog.

As the prototype, the ESS is taken which osmolarity value corresponds to that of the blood plasma of a particular patient, which enables to prevent disorders of the organism water balance when conducting intestinal lavage [Patent for Invention RU 2190412]. A change of solution osmolarity either toward an increase or a decrease is effected by changing a concentration of salts therein. Solutions with different concentrations may be prepared by dissolving different quantities of salts in a given amount of water, which is inconvenient in the conditions of mass production, or dissolving a given quantity of salts in different volumes of water, which seems to be more ergonomic.

The authors of the above invention propose to calculate a water volume required for dissolving a given quantity of salts according to the provided formula in order to prepare a solution having a required osmolarity value corresponding to the blood plasma osmolarity. Moreover, it is necessary to know an initial value of colloid-osmotic pressure of the blood plasma. A value of a water volume required for preparing the solution is inversely proportional to a value of colloid-osmotic pressure of the blood plasma.

A disadvantage of this technical solution is that, in order to prepare a solution with a given osmolarity corresponding to that of the blood plasma of a particular patient, in each case it is required to conduct a laboratory analysis of the patient's blood for determining this parameter, which is possible only in the conditions of a medical facility provided with a laboratory. It is not feasible in ambulatory, field and home conditions. Moreover, this approach precludes the possibility of mass production of a solution ready for use. Another disadvantage of this solution is that it is not stable and quickly becomes turbid, and a sediment appears; furthermore, if a salt concentration is increased for increasing osmolarity of the solution, its storage life is reduced even more. Moreover, there are no data that the prototype solution facilitates acceleration of the GIT mucosa regeneration if the latter is damaged or becomes inflamed.

SUMMARY OF THE INVENTION

The technical objective achieved by the claimed invention is to develop a composition of an enteral solution usable for lavage of the gastrointestinal tract and for correcting homeostasis disorders, which is deprived of the disadvantages typical for the above analogs.

The technical effect of the claimed invention is maintenance of qualitative characteristics of the acid-mineral composition (AMC) in the form of a dry powder and a ready-for-use solution for a long storage period (at least 1 year) and during heating of a solution, while ensuring its usability as a medicine facilitating regeneration of the GIT mucosa. The proposed enteral solution may be also used for prophylaxis of edemas. The AMC and the composition of the enteral solution are universal for lavage of the gastrointestinal tract in patients and/or for correcting homeostasis disorders.

This technical result is achieved owing to that, in order to prepare the proposed acid-mineral compositions (AMCs) and the enteral solution, mono-, or twice-, or triple-substituted sodium phosphate, or mono- or twice-substituted potassium phosphate, sodium chloride, sodium acetate (or without it), potassium chloride, calcium chloride, magnesium sulphate, citric acid (or without it) are used; and purified drinking water is used for preparing the enteral solution from the AMC in such a range of volumes that the dissolved salts and acids can provide a solution osmolarity from 280 to 310 mOsm/L; moreover, the AMC and the solution further comprise aminopolycarboxilic acid preventing insoluble salts from forming in the solution and short-chain carboxylic (fatty) acids in a quantity providing a solution pH value in the range from 4.61 to 5.8.

One out of the six equivalent variants is used for preparing the AMC and the proposed enteral solution (Tables 1 and 2):

TABLE 1

Formulation variants of the acid-mineral compositions (AMCs)

Formulation variants Ingredients B wt % to AMC total weight

| Ingredients | I | II | III | IV | V | VI |
|---|---|---|---|---|---|---|
| Sodium phosphate, triple-substituted, 12-aqueous. | 35.7-40.48 | — | — | — | — | — |
| Sodium phosphate, twice-substituted, 12-aqueous. | — | 33-36.48 | — | — | — | — |
| Sodium phosphate, twice-substituted, anhydrous. | — | — | — | — | — | 16.85-19.09 |
| Sodium phosphate, mono-substituted, anhydrous. | — | — | 16.29-17.92 | — | 5.99-6.71 | — |
| Sodium chloride | 17.68-20.03 | 20.24-22.34 | 22.34-24.59 | 29.63-32.73 | 30.82-34.5 | 25.13-28.46 |
| Sodium acetate, 3-aqueous. | — | 4.0-4.43 | 18.76-20.64 | 19.32-21.35 | 9.72-10.88 | 4.98-5.64 |
| Potassium chloride | 9.52-10.79 | 9.08-10.03 | 10.03-11.04 | 2.24-2.47 | — | 11.28-12.78 |
| Potassium phosphate, mono-substituted. | — | — | — | 14.91-16.48 | — | — |
| Potassium phosphate, twice substituted, 3-aqueous. | — | — | — | — | 15.51-17.36 | — |
| Calcium chloride | 9.27-10.5 | 8.85-9.77 | 9.77-10.75 | 10.17-11.24 | 9.99-11.18 | 10.99-12.45 |
| Magnesium sulphate | 7.73-8.75 | 7.37-8.14 | 8.14-8.96 | 8.47-9.36 | 8.32-9.31 | 9.16-10.37 |
| Na2EDTA or Na3DTPA | 1.5-5.8 | 1.47-5.4 | 1.63-5.95 | 1.69-6.22 | 1.66-6.18 | 1.83-6.89 |
| Citric acid, anhydrous | 3.1-7.0 | 2.95-4.56 | — | — | 3.33-5.22 | 3.66-5.81 |
| Lactic acid | 1.48-4.9 | 1.4-4.56 | 1.56-5.0 | 1.63-5.24 | 1.6-5.22 | 1.76-5.81 |
| Propionic acid | 1.48-3.36 | 1.4-3.13 | 1.56-3.44 | 1.63-3.59 | 1.6-3.58 | 1.76-3.98 |
| Butyric acid | 0.74-1.68 | 0.71-1.56 | 0.78-1.72 | 0.81-1.8 | 0.8-1.79 | 0.88-1.99 |

TABLE 2

Formulation variants of the proposed enteral solution

Formulation variants Ingredients B wt % to total weight of solution

| Ingredients | I | II | III | IV | V | VI |
|---|---|---|---|---|---|---|
| Sodium phosphate, triple-substituted, 12-aqueous. | 0.63-0.754 | — | — | — | — | — |
| Sodium phosphate, twice-substituted, 12-aqueous. | — | 0.61-0.73 | — | — | — | — |
| Sodium phosphate, twice-substituted, anhydrous. | — | — | — | — | — | 0.252-0.301 |
| Sodium phosphate, mono-substituted, anhydrous. | — | — | 0.273-0.327 | — | 0.098-0.118 | — |
| Sodium chloride | 0.31-0.37 | 0.375-0.45 | 0.375-0.448 | 0.478-0.571 | 0.507-0.605 | 0.376-0.449 |
| Sodium acetate, 3-aqueous. | — | 0.074-0.089 | 0.315-0.376 | 0.312-0.373 | 0.16-0.191 | 0.075-0.089 |
| Potassium chloride | 0.168-0.2 | 0.168-0.2 | 0.168-0.2 | 0.036-0.043 | — | 0.169-0.202 |
| Potassium phosphate, mono-substituted. | — | — | — | 0.241-0.288 | — | — |
| Potassium phosphate twice-substituted, 3-aqueous. | — | — | — | — | 0.255-0.304 | — |
| Calcium chloride | 0.164-0.196 | 0.164-0.196 | 0.164-0.196 | 0.164-0.196 | 0.164-0.196 | 0.164-0.196 |
| Magnesium sulphate | 0.137-0.163 | 0.137-0.163 | 0.137-0.163 | 0.137-0.163 | 0.137-0.163 | 0.137-0.164 |
| Na2EDTA or Na3DTPA | 0.029-0.117 | 0.029-0.117 | 0.029-0.118 | 0.03-0.118 | 0.03-0.118 | 0.03-0.118 |
| Citric acid, anhydrous | 0.055-0.13 | 0.055-0.091 | — | — | 0.055-0.091 | 0.055-0.092 |
| Lactic acid | 0.026-0.091 | 0.026-0.091 | 0.026-0.091 | 0.026-0.091 | 0.026-0.091 | 0.026-0.092 |
| Propionic acid | 0.026-0.063 | 0.026-0.063 | 0.026-0.063 | 0.026-0.063 | 0.026-0.063 | 0.026-0.063 |
| Butyric acid | 0.013-0.031 | 0.013-0.031 | 0.013-0.031 | 0.013-0.031 | 0.013-0.031 | 0.013-0.031 |
| Purified drinking water | 97.9-98.4 | 97.78-98.35 | 97.98-98.47 | 98.06-98.54 | 98.03-98.53 | 98.2-98.68 | according to the first variant, the AMC and the enteral solution comprise sodium phosphate triple-substituted, sodium chloride, potassium chloride, citric, lactic, propionic and butyric acids, a complexon, e.g. Na2EDTA or Na3DTPA, as well as calcium chloride and magnesium sulphate;

according to the second variant, the AMC and the enteral solution comprise sodium phosphate twice-substituted, sodium chloride, sodium acetate, potassium chloride, citric, lactic, propionic and butyric acids, a complexon, e.g. Na2EDTA or Na3DTPA, as well as calcium chloride and magnesium sulphate;

according to the third variant, the AMC and the enteral solution comprise sodium phosphate mono-substituted, sodium chloride, sodium acetate, potassium chloride, lactic, propionic and butyric acids, a complexon, e.g. Na2EDTA or Na3DTPA, as well as calcium chloride and magnesium sulphate;

according to the fourth variant, the AMC and the enteral solution comprise potassium phosphate mono-substituted, sodium chloride, sodium acetate, potassium chloride, lactic, propionic and butyric acids, a complexon, e.g. Na2EDTA or Na3DTPA, as well as calcium chloride and magnesium sulphate;

according to the fifth variant, the AMC and the enteral solution comprise sodium phosphate mono-substituted, sodium chloride, sodium acetate, potassium phosphate twice-substituted 3-aqueous, citric, lactic, propionic and butyric acids, a complexon, e.g. Na2EDTA or Na3DTPA, as well as calcium chloride and magnesium sulphate;

according to the sixth variant, the AMC and the enteral solution comprise sodium phosphate twice-substituted, sodium chloride, sodium acetate, potassium chloride, citric, lactic, propionic and butyric acids, a complexon, e.g. Na2EDTA or Na3DTPA, as well as calcium chloride and magnesium sulphate.

In all the AMC variants, calcium chloride and magnesium sulphate are isolated from each other and from a mixture of the remaining ingredients. The ingredient ratios in the AMC for all the six variants are presented in Table 1; the ingredient ratios in the enteral solution for all the six variants are presented in Table 2, in wt %.

The invention uses anhydrous acids: propionic, butyric (liquids) and citric acid (powder) as well as lactic acid 80%.

The proposed technical solution provides the enteral solution with additional properties owing to which its use for IL facilitates shortening of a regeneration period of the GIT mucosa when it is damaged and becomes inflamed, and, as a consequence of accelerated regeneration of the GIT mucosa, lowering of a rate of extraintestinal infectious complications caused by hyperpermeability of the intestinal barrier.

The claimed composition of the proposed solution is characterized by an increase in an storage life of the enteral solution (within a period corresponding to consumer property of the commodity) and by the possibility of heating up to 37-40° C. with maintenance of its properties, which precludes its turbidity and formation of a sediment therein, when regeneration of the GIT epithelial cells is accelerated. These properties are provided through changing the qualitative and quantitative composition of the components, including changes caused by adding short-chain fatty acids (SCFAs) and aminopolycarboxylic acids into the solution, which block the interaction of cations and anions capable of forming insoluble salts in the solution.

The claimed composition does not provoke edemas in patients after intestinal lavage (and may be used, inter alia, for prophylaxis of edemas) due to the use of the solution quasi-osmotic to the blood plasma, which osmolarity values cover the range of physiological indices (280-310 mOsm/kg) of the blood plasma osmolality, making a pre-determination of a patient's plasma osmolality optional before IL, but this is obligatory if the prototype is used.

The enteral solution, which is isoionic to chyme and quasi-osmotic to the blood plasma, comprises sodium phosphate mono- or twice-, or triple-substituted, or potassium phosphate mono- or twice-substituted, sodium chloride, sodium acetate, potassium chloride, calcium chloride, magnesium sulphate, citric acid (or without it), purified drinking water, and, additionally, complexons in a quantity sufficient for blocking cations Ca2+ and Mg2+ in the solution, in particular, aminopolycarboxylic acids (APCA) or their salts, e.g., a disodium salt of ethylenediaminetetraacetic acid (Na2EDTA, or "Trilon B"), or a trisodium salt of diethylenetriaminepentaacetic acid (Na3DTPA), or iminodiacetic acid, or nitrilotriacetic acid.

The APCA, e.g., Na2EDTA and Na3DTPA, are capable of forming stable and poorly dissociating complexes with bi-, tri- and tetravalent cations, in the case under consideration—with cations Ca2+, forming, respectively, CaNa2EDTA (tetacinum) and CaNa3DTPA (pentacinum), and with cations Mg2+, preventing their interaction with anions SO42− and PO43− in a salt solution and, thus, preventing formation of water-insoluble salts: CaSO4, Ca3(PO4)2 and MgHPO4. Further, they do not change a solution pH value and do not lower concentrations of calcium and magnesium in the blood, they are quickly removed from the organism with urea and are metabolized in the kidneys until carbon dioxide is formed. They withdraw heavy metals and free radicals from the organism.

A solution comprising tetacinum or pentacinum may be heated and stored for a long time. The storage life of the solution depends on the concentrations of these complexons. In order to bind cations, e.g. calcium, in the solution, an equivalent quantity of Na2EDTA or Na3DTPA is required. It is known that the proposed complexons are intended for parenteral introduction, since they are poorly absorbed from the GIT, namely, only 2-5% of their total amount taken orally enter into the blood [Semenov D. I., Tregubenko I. P. Complexons in Biology and Medicine/Sverdlovsk: UNTs of USSR AS, 1984.—281 P.//Access to: https://www.i-pae.uran.ru/sites/default/files/Complexons.pdf]. The single therapeutic dose at intravenous introduction is 2 g, and the daily dose is 4 g [Mashkovsky M. D. Medicinal Agents. In 2 volumes. V. 2. 11th edition. ster.—M.: Medicine, 1988. p. 186.]. The proposed solution, which comprises Na2EDTA or Na3DTPA, is intended for oral intake. Calculations show that the single dose of 2 g at intravenous introduction is equivalent to the dose of 40 g at oral intake of Na2EDTA or Na3DTPA.

In order to find out how a storage life duration of the solution depends on a concentration of Na2EDTA comprised therein, we conducted studies that showed that a concentration of Na2EDTA in the range from 0.07 to 0.09%, which corresponds to specific content of 0.029-0.118 wt % in the formulations 1-6 of the proposed solution, provides its stabilization for 1-4 years. Within the observation period, the solution remained clear and did not have a sediment. At lower concentrations of Na2EDTA in the solution (Table 3), the solution became turbid and has a sediment. The storage life of 1-4 years with keeping the solution sterile complies with the conditions of its serial production and mass consumption.

Dependence of enteral solution storage lives on concentrations of Na2EDTA contained therein is presented in Table 3.

TABLE 3

Dependence of storage life of the proposed solution on Na2EDTA concentration Na2EDTA concentration in the solution (formulation variants 1-6) Solution storage life*

| | |
|---|---|
| 0 | 1-3 days |
| 0.027 | 5 days |
| 0.036 | 7 days |
| 0.04 | 17 days |
| 0.05 | 30 days |
| 0.06 | 6 months |
| 0.07 | app. 1 year |
| 0.09 | up to 4 years. |

Note:
*the indicated storage lives of the solution are determined at the room temperature under light.
The observation period is 4 years.

Heating of the solution comprising 0.07-0.09% of Na2EDTA up to 40° C. does not cause its becoming turbid, as opposed to the prototype solution. A Na2EDTA concentration less than 0.07% does not ensure turbidity of the solution when it is heated.

Depending on indications, an IL procedure may be conducted with an ESS volume from 4 to 30 L [Matkevich V. A. Intestinal Lavage//Medical Toxicology: National Manual/ ed. by Ye. A. Luzhnikov. M.: GEOTAR-Medicine, 2012.—Ch. 4.—pp. 162-186].

Calculations show that, in order to prepare the solution in the volume of 30 L, 27.0 g of Na2EDTA is required for producing the concentration of 0.09%, a part of this quantity, which is equal to 5%, which will be included into the resorption process, is equal to 1.35 g, which is less than the single therapeutic dose at intravenous introduction. This volume of the solution is quite sufficient for conducting the IL procedure for patients with a severe somatic status. If the patient's condition is satisfactory, a lesser volume of the solution, e.g., 4.5 L, is required, wherein, at the concentration of 0.09%, 4.05 g of Na2EDTA are contained, and 5% of this quantity are 0.2 g. In practice, during intestinal lavage app. 90% of the solution volume introduced into the GIT are removed in the natural way. Consequently, the Na2EDTA content of a solution part remaining in the patient's body is $\frac{1}{10}$ of the total quantity. Such doses of the proposed complexons are safe for the patient. CaNa2EDTA and CaNa3DTPA are well soluble in water, and, therefore, their part that enters the blood is easily removed from the organism through the kidneys [Semenov D. I., Tregubenko I. P. Complexons in Biology and Medicine/Sverdlovsk: UNTs of USSR AS, 1984-281 P.//Access to: https://www.i-pae.uran.ru/sites/default/files/Complexons.pdf; Zorina L. A. Modern State of the Issue of Using CaNa2EDTA at Lead Intoxication in Clinics.—Labot Hygiene—1963—No. 8.—pp. 9-14.].

Furthermore, the enteral solution further contains a SCFA complex in a quantity providing a solution pH value in the range from 4.61 to 5.8 at its specific weight ratio in the mixture close to the physiological one.

Experimentally, it is established that addition of acids into the proposed solution, such as lactic, propionic and butyric acids, in a quantity of 0.026-0.092, 0.026-0.063 and 0.013-0.031 wt %, respectively, will acidify it to pH values in the range from 4.61 to 5.8. Addition of these acids in a quantity greater than indicated is associated with lowering of the solution pH value below 4.61, which is not physiological for the bowels, and, taking into account that big volumes are required for conducting an IL procedure, it may negatively affect the patient's condition.

The selection of acid concentrations and their ratio in the mixture is made with due regard to the permissible norms of using these acids in the food industry and their physiological content in the intestinal cavity. According to T. D. Bokova, N. I. Ursova and M. D. Ardatskaya (2008), the reference values of propionic and butyric acids are 1.79±0.95 and 1.75±0.85 mg per 1 g of feces, respectively [T. D. Bokova, N. I. Ursova, M. D. Ardatskaya. Disorders of the Spectrum of Short-Chain Fatty Acids in Children with Obesity, and their Correction with the Use of Normoflorin-D//Access to: http://normoflorin.ru/disorders-spectrum-short-chain]. At such concentration values, app. 0.25-0.8 g of propionic acid and 0.27-0.78 g of butyric acid are removed in the result of a single physiological bowel emptying, which amounts only to 5% of their total pool in the bowels [Shenderov B. A. Targets and Effects of Short-Chain Fatty Acids//Sovremennaya Meditsinskaya Nauka 2013, No. 1-2 Access to: https://www.researchgate.net/publication/286456237_Effekty_i_miseni_letucih_ztrnyh_kislot].

Lactic (α-oxypropionic) acid is a natural product and may be considered as a biologically safe product, since it is a natural metabolite of the human organism, animals and plants, exhibits a strong antimicrobial effect, the capability of suppressing a growth of the putrefactive microflora in the bowels, reducing formation of toxic products of organic substance decomposition in the organism, improving the metabolic processes, regulate pH. Lactic acid of the food grade does not have contraindications and is permitted in diets at various diseases of the kidneys, the gallbladder and the pancreas.

SCFAs are natural metabolites forming in the bowels in the process of processing oligo- and polysaccharides by the saccharolytic microflora. While acidifying the intestinal medium, they, thereby, display their antagonism in relation to the proteolytic microflora, including the conditionally pathogenic flora, suppressing its growth [Shenderov B. A., Medicinal Microbial Ecology and Functional Nutrition: in 3 Volumes/Shenderov B. A.—M.: GRANT, 1998.—V. I: Microflora of Human Being and Animals and Its Functions.—288 pp.]. When a pool of the conditionally pathogenic flora is reduced, its virulence and invasiveness is decreased. Thus, a solution, which is enriched with SCFAs, exhibits pre-biotic properties facilitating prophylaxis and elimination of inflammatory processes in the bowels.

Another key point is that, unlike the main mass of eukaryotic cells which receive nutrients solely through the circulatory system, the epithelial cells of the GIT mucosa receive, in their major part, nutrition from the GIT cavity in the form of SCFAs that are, for these cells, the exclusive food (energy) substrate. States characterized by a food substrate deficit provoke atrophy of the GIT mucosa. SCFAs, as contained in the proposed enteral solution, may be used by the intestinal epithelial cells as an additional source of energy. Provision of an adequate additional food resource in the conditions of its initial deficit facilitates a growth of epithelial cells and, consequently, accelerated regeneration of the mucosa and healing of its defects.

The process of regeneration of the intestinal mucosa wholeness in cases of its damage and inflammation is, in its turn, extremely important for preventing and correcting the syndrome of hyperpermeability of the intestinal barrier for microbial toxins and pathogens themselves, other biologically active pathologic substances that may enter the inner medium of the organism, including the systemic blood flow. Normalization of intestinal permeability facilitates reduction of the risk that extraintestinal complications of inflammatory nature, including pneumonia, may develop.

In the proposed solution, a water mass amounting to, depending on the formulations of the six variants, 97.78-98.68 wt % of the total solution weight, pre-conditions the concentration of the salts and the acids to which a solution osmolarity in the range from 280 to 310 mOsm/L. The solution osmolarity depends on the concentration of the salts and the acids, and their concentration, at their identical weight values, is in inverse relationship with an amount of water required for their dissolution. Owing to the solution osmotic pressure close (quasi-osmotic) to the physiological values of the colloid-osmotic pressure of the blood plasma, excess entry of water into the bloodstream from the GIT is prevented, due to which the risk of edemas is reduced. If a patient is disposed to edemas, it is reasonable to conduct an IL procedure with a solution having the maximum osmolarity value, i.e. 310 mOsm/L. At solution osmolarity values greater than 310 mOsm/L, the risk of water deficit in the organism after an IL procedure appears, since water moves from the bloodstream into the GIT cavity and then, in the form of diarrhea, outside [Matkevich V. A. Intestinal Lavage//Medical Toxicology: National Manual/ed. by Ye. A. Luzhnikov. M.: GEOTAR-Medicine, 2012.—Ch. 4.—pp. 162-186].

BRIEF DESCRIPTION OF THE DRAWINGS

The invention is explained by the illustrative materials which present a pattern of accelerated regeneration of a particular patient's GIT mucosa (according to the results of clinical observation), owing to the use of the proposed solution.

BEST MODE OF CARRYING OUT THE INVENTION

Figure 1:
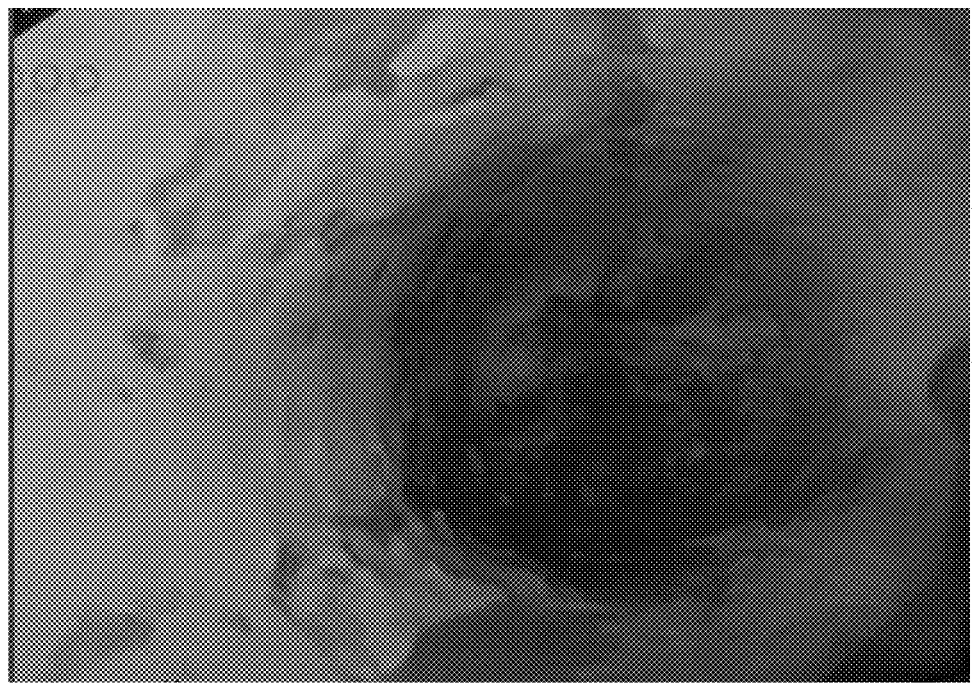
FIG. 1/5 shows the pattern of damage caused to the mucosa at esophagus parts (chemical burn) of the patient before starting the treatment.

Preparation of the AMC and the Enteral Solution (ES)

The proposed solution may be prepared either in the ready-to-use form, or as a semi-finished product, i.e. an AMC set (comprising concentrates of all the ingredients, magnesium sulphate (in the form of powder or solution) and a calcium chloride solution being isolated from the other components). In the latter case, the user may prepare the solution himself, following the accompanying instructions. The AMC may be prepared as a series for a certain volume of the solution, e.g., 4.5 or 30 L, etc.; in this case, the total weight of the ingredients and the calculated volume of water are indicated.

The enteral solution may be prepared from the AMC in the following way. The AMC, except for the magnesium and calcium salts, is dissolved in two thirds of the stipulated volume of purified drinking water, then magnesium sulphate (in the form of powder or solution) and calcium chloride (in the form of solution) are added. After this, purified drinking water is added until the preset volume is reached.

The proposed solution is used as follows.

I. Intestinal Lavage

A minimal volume of the solution, which is required for effective irrigation of the GIT of an adult patient, is 3.0-4.5 L per one procedure. The intestinal lavage should be carried out on an empty stomach (a fasting period should be at least 5-6 hours). The procedure, especially the first one, should be conducted, preferably, in the morning. The solution is heated (up to 37-40° C.) before use.

The patient should drink the solution by portions of 150-200 mL every 5 minutes. Usually, the bowels start emptying by itself also by portions, after patients drink 1.5-2.5 L of the solution. The procedure should be continued until a time when excrements become clear (may have a yellowish color), then the patient stops drinking the solution, but defecation may continue for the following 30-40 minutes; then intestinal discharge stops. After 1-1.5 hours, the patient should receive food rich in edible fibers (porridges made of whole unpolished cereals with water without sugar, dried apricots). Later, the patient resumes taking food as usual, except for spicy and fatty foods, smoked products and alcohol within 2-3 days.

An average duration of the procedure is 3 hours. After an IL procedure, a patient may be engaged in usual business, without being concerned about diarrhea recurrence.

In cases where patients, due to their severe condition, may not take the solution on their own, specialists introduce it through a tube.

Indications for Intestinal Lavage:
1. Exo- and endotoxicosis;
2. Intestinal disbiosis;
3. Acute and chronic hepatitis;
4. Acute and chronic pancreatitis;
5. Gastritis, enterocolitis;
6. Dyskinesia of the biliary tracts;
7. Constipation of I*III degree, having the functional nature;
8. Infectious intestinal diseases;
9. Chronic pyelonephritis;
10. Diseases accompanied by skin damage (atopic dermatitis, neurodermatitis, psoriasis, eczema, acne, etc.);
11. Acute and chronic allergic diseases;
12. Bronchial asthma, inflammatory non-specific bronchopulmonary diseases;
13. Diseases associated with hormonal disorders and metabolic disorders, including calcinosis (dermatomyositis, scleroderma, myositis ossificans), pathological skeleton ossification, arthritis with salt deposition, calcium deposition in the kidneys;
14. Alcohol withdrawal syndrome, drinking bout, abstinence syndrome (including alcoholic hallucinosis, delirium);
15. Chronic inflammatory diseases of small pelvis organs;
16. Post-operational and traumatic enteroparesis;
17. Burn disease;
18. Radiation sickness;
19. Oncological diseases;
20. Preparations for planned operations and endoscopic examinations;
21. Gas gangrene.

For prophylaxis of diseases, the IL procedure is recommended to patients:
after stresses, with errors in rations, whose ration comprises insufficient amount of fibers, practicing disorderly meals, having sedentary mode of life, disposed to obesity, subject to frequent catarrhal diseases, engaged in production with factors harmful for health, having bad habits.

Absolute contraindications are: intestinal obstruction of mechanical etiology (intestinal tumors, intestine scarry stricture, mechanical intestine squeezing from outside, etc.), gastrointestinal and other internal hemorrhages, threat and perforation of the GIT hollow organ, acute appendicitis, pregnancy second half, hypertensic crisis, acute cardiovascular pathology and pulmonary decompensation.

Relative contraindications are: cholelithiasis and urolithiasis, diabetes of I type, acute condition of hemorrhoid, pregnancy first half, hemophilia.

II. Nutritional Correction

A patient takes the solution by portions (e.g., 200 mL) for 1 day, the total volume is up to 1.5 L. If the solution is taken in a volume greater than 1.5 L, diarrhea may appear in an adult patient, i.e. the effect of intestinal lavage may come out.

Indications:
1. Deficit of electrolytes in the organism (e.g. their loss with excessive sweat, during diarrhea associated with an intestinal infection, etc.);
2. Functional disorders of the gastrointestinal tract;
3. Acidosis, including that in sportsmen during a period of intensive physical loads; at alcohol withdrawal syndrome;
4. Shock, including post-hemorrhagic shock;
5. Radiation sickness;
6. Post-operational period.

The claimed properties of the proposed solution are confirmed by the results of the studies conducted.

Nineteen male patients aged from 37 to 85, having severe intoxications by cauterizing liquids were observed. In 11 cases, intoxication was provoked by oral intake of a base, in 8 cases—a concentrated acetic acid. Chemical burns of the mucosa of mouth, pharynx, esophagus and stomach were identified in the result of the endoscopic examination—esophagogastroduodenoscopy (EGDS). Out of the total number of the patients, 13 have a stomach burn of 2-3 degree, 6 have a stomach burn of 3-4 degree. For 11 patients, including three with a stomach burn of 3-4 degree, intestinal lavage with the use of the proposed solution was included into a complex of medicinal measures (the observed group). The comparison group consisted of 8 patients receiving the standard therapy, who were subjected to the IL procedure with the use of an ESS (prototype).

The patients of the observed group were given 200 mL of the proposed solution every 5 minutes in the initial hours of the chemical trauma after administration of anesthetics and spasmolytics and tube lavage of the stomach. With due regard to the specifics of the intoxication (risk of hemorrhage), in these cases the solution was not heated, its temperature was 18-22° C. Diarrhea in patients appeared in 1.5-2 hours. The GIT was irrigated until light, semitransparent waters appeared from the rectum. The total volume of the solution was in the range from 3 to 4.5 L. The patients tolerated the IL procedure satisfactorily, no reactions and complications were identified. On the following days, the patients were given the same solution orally by 200-mL portions with the total volume of 1.5-3 L daily as nutritional correction.

The comparative assessment of the treatment results showed that clearly positive dynamics of the process of cleansing the damaged parts of the esophagus and stomach mucosa was recorded on Day 5, namely, necrotic masses disappeared, the thickness of fibrin layups decreased, areas of granulations appeared. By that time, no signs of regeneration of local defects on the esophagus and stomach mucosa were recorded. The pneumonia rate in the observed group and the comparison group was 18.2 and 37.5%, respectively. Two patients died in the comparison group, and the patients of the observed group remained alive, and an average hospitalization period of the latter was reduced by 25% in comparison with the former.

Thus, the use of the proposed solution in the complex therapy of cauterizing liquid intoxications facilitates acceleration of healing damaged areas of the mucosa, reduction of a pneumonia rate as a complication of intoxication by 48.5% and decrease of an average hospitalization period.

The following clinical observation may serve as an example of accelerated regeneration of the GIT mucosa owing to the use of the proposed solution.

Patient D. aged 44. Diagnosis: intoxication by acetic essence dated 17 Jan. 2017.

The first EGDS examination was conducted on 18 Jan. 2017 when the patient was taken to the hospital.

The description of the EGDS pattern: the esophagus mucosa was apparently edematous, with confluent circular layups of light fibrin of various densities. Multiple erosions were visible. The stomach mucosa was hyperemic, edematous with multiple acute erosions up to 0.2 cm in diameter with a clean bottom. The duodenum mucosa had confluent layups of light fibrin. The postbulbar mucosa was also hyperemic, edematous; multiple linear ulcerous defects with a clean bottom, which had a depth up to 0.2 cm, and linear erosions with a clean bottom were detected.

Conclusion: disseminated erosive-ulcerous burn esophagitis, disseminated erosive burn gastritis, disseminated ulcerous burn duodenitis.

FIG. 1 shows a pattern of damaged mucosa of esophagus parts (chemical burn) of a patient before start of the treatment.

In addition to a complex of standard therapy, on the first day the patient was subjected to an IL procedure following the above methodology with the use of the proposed solution in the volume of 4.5 L which was prepared according to the second variant of the formulation (specific weight of the ingredients in wt %): sodium phosphate, twice-substituted, 12-aqueous—0.61; sodium chloride—0.375; sodium acetate, 3-aqueous—0.074; potassium chloride—0.168; acids: citric—0.055, lactic—0.026, propionic—0.026 and butyric—0.013; Na2EDTA—0.029, calcium chloride—0.164; magnesium sulphate—0.137 and purified drinking water—98.35.

During the following 5 days, the same solution was administered to the patient orally, by 200-mL portions with the total volume of 2-3 L per day as the nutritional correction. No complications and side effect were recorded, the patient tolerated the solution intake well. The patient's status was improved, normalization of the water-electrolytic balance was recorded. On Day 5 of the medical measures, the patient was subjected to the second EGDS.

Description of the EGDS Pattern Dated 23 Jan. 2017:

Clearly positive dynamics of the burn surface condition: the esophagus—the mucosa is moderately edematous; fibrin is fragmented in the upper third; confluent circular layups of light fibrin of various densities remain in the middle third of the esophagus; the mucosa was cleaned from fibrin on the part from 35 to 40 cm. The esophagus mucosa is hyperemic, moderately edematous; the erosions were epithelized. The duodenum mucosa is hyperemic, edematous, ulcerous defects were cicatrized.

Figure 2:
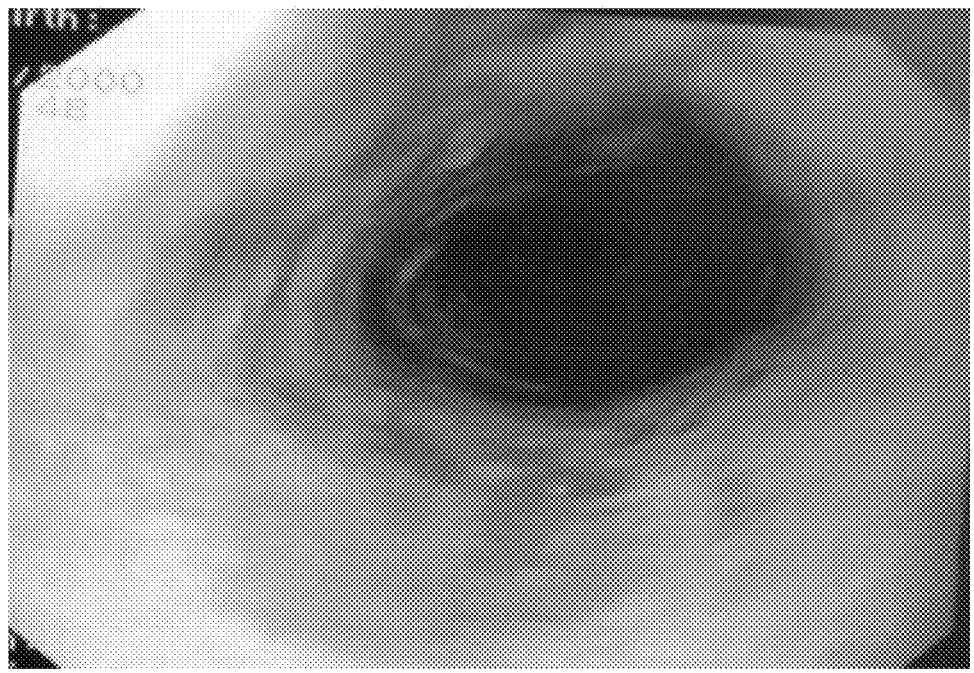
FIGS. 2/5 and 3/5 show a pattern of the mucosa condition at various parts of the esophagus in 5 days.
Figure 3:
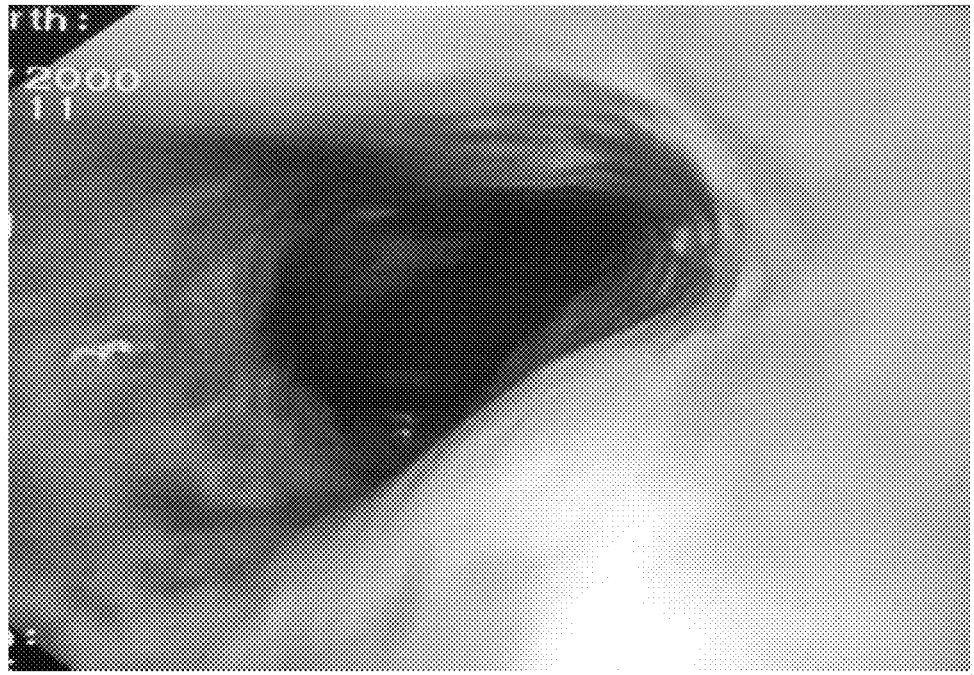
Figure 4:
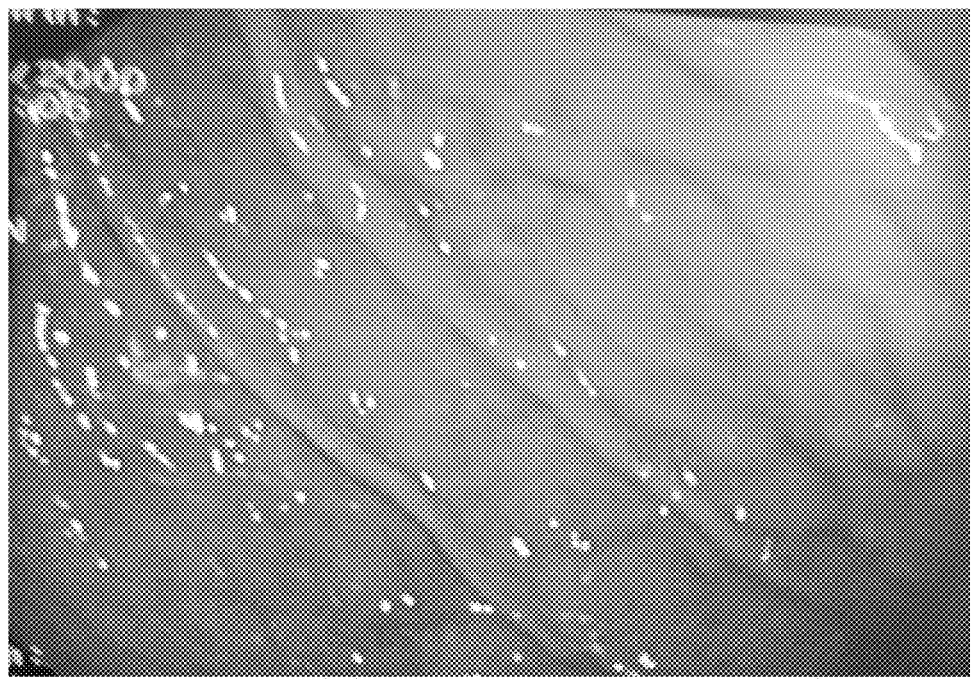
FIGS. 4/5 and 5/5 show the condition of the mucosa of the stomach and the duodenum, respectively, after the same period.
Figure 5:
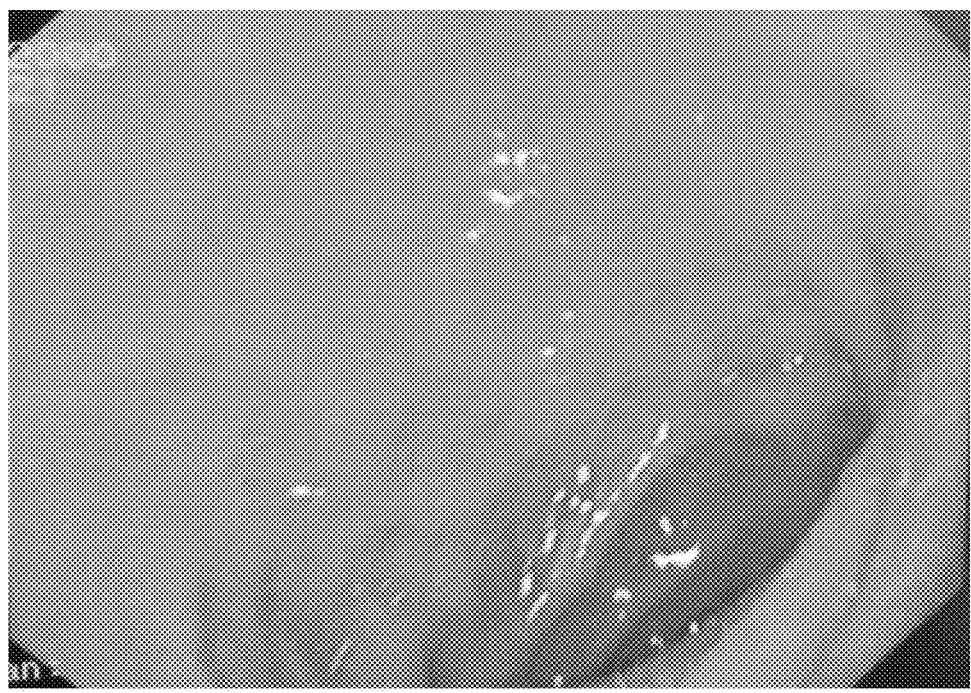

FIGS. 2 and 3 show the pattern of the mucosa condition at various parts of the esophagus in 5 days. FIGS. 4 and 5 show the condition of the mucosa of the stomach and the duodenum, respectively, after the same period.

The disease course was smooth, without complications, and resulted in the recovery.

The proposed technical solution is new, since it is not obvious from the state of the art. It has a significant distinction from the prototype, namely, it ensures a long storage period of the solution (for more than 1 year) and maintenance of its properties at heating due to preventing insoluble salts from forming therein; it ensures edema prophylaxis after an intestinal lavage procedure without the necessity of conducting an obligatory laboratory study of a blood plasma osmolality due to the range of solution osmotic pressure covering the physiological values of the blood plasma osmolality, which precludes excess enter of water into the blood from the GIT cavity during an IL procedure, facilitates shortening of a regeneration period of the gastrointestinal tract mucosa when it is damaged and inflamed, reduction of a rate of extraintestinal complications associated with hyperpermeability of the intestinal barrier due to prebiotic properties of the solution.

The improved consumer qualities of the proposed solution enable to produce it serially, store for a long time and transport, use not only in specialized medical facilities, but also in other facilities as well as in the ambulatory and field conditions, which expands the field of its applicability being more practically feasible and more ergonomic, as compared to the prototype.

What is claimed is:

1. An acid-mineral composition for producing an enteral solution for a lavage of a gastrointestinal tract and/or a correction of homeostasis disorders, comprising:
    a mixture of sodium, potassium, calcium and magnesium salts, each of which is present in a quantity providing mineralization of the enteral solution in a range from 10.7 g to 14.0 g per 1 L of the enteral solution;
    an aminopolycarboxylic acid (APCA) salt in a quantity preventing insoluble salts of calcium and magnesium from forming in the enteral solution, the APCA salt comprising one of a disodium salt of ethylenediaminetetraacetic acid (Na2EDTA) and a trisodium salt of diethylenetriaminepentaacetic acid (Na3DTPA); and
    a short-chain fatty acid (SCFA) complex in a total quantity sufficient for maintaining a pH of the enteral solution in a range from 4.61 to 5.8;
    wherein the SCFA complex comprises one of:
        a first complex comprising lactic, butyric and propionic acids, and
        a second complex comprising lactic, butyric, propionic and citric acids;
    wherein, in case of the first complex, the mixture of sodium, potassium, calcium and magnesium salts comprises one of:
        a first mixture comprising mono-substituted sodium phosphate, sodium chloride, sodium acetate, potassium chloride, calcium chloride and magnesium sulphate; and
        a second mixture comprising sodium chloride, sodium acetate, potassium chloride, mono-substituted calcium phosphate, calcium chloride and magnesium sulphate;
    wherein, in case of the second complex, the mixture of sodium, potassium, calcium and magnesium salts comprises one of:
        a third mixture comprising triple-substituted sodium phosphate, sodium chloride, potassium chloride, calcium chloride and magnesium sulphate;
        a fourth mixture comprising twice-substituted sodium phosphate, sodium chloride, sodium acetate, potassium chloride, calcium chloride and magnesium sulphate;
        a fifth mixture comprising mono-substituted sodium phosphate, sodium chloride, sodium acetate, twice-substituted potassium phosphate, calcium chloride and magnesium sulphate; and
        a sixth mixture comprising twice-substituted sodium phosphate, sodium chloride, sodium acetate, potassium chloride, calcium chloride and magnesium sulphate;
    wherein a weight percent of each component in the acid-mineral composition is as follows:
        in case of the first complex and the first mixture:
            mono-substituted sodium phosphate, anhydrous—16.29-17.92;
            sodium chloride—22.34-24.59;
            sodium acetate, 3-aqueous—18.76-20.64;
            potassium chloride—10.03-11.04;
            calcium chloride—9.77-10.75;
            magnesium sulphate—8.14-8.96;
            Na2EDTA or Na3DTPA—1.63-5.95;
            lactic acid—1.56-5.0;
            propionic acid—1.56-3.44;
            butyric acid—0.78-1.72;
        in case of the first complex and the second mixture:
            sodium chloride—29.63-32.73;
            sodium acetate, 3-aqueous—19.32-21.35;
            potassium chloride—2.24-2.47;
            mono-substituted potassium phosphate—14.91-16.48;
            calcium chloride—10.17-11.24;
            magnesium sulphate—8.47-9.36;
            Na2EDTA or Na3DTPA—1.69-6.22;
            lactic acid—1.63-5.24;
            propionic acid—1.63-3.59;
            butyric acid—0.81-1.8;
        in case of the second complex and the third mixture:
            triple-substituted sodium phosphate, 12-aqueous—35.7-40.48;
            sodium chloride—17.68-20.03;
            potassium chloride—9.52-10.79;
            calcium chloride—9.27-10.5;
            magnesium sulphate—7.73-8.75;
            Na2EDTA or Na3DTPA—1.5-5.8;
            citric acid, anhydrous—3.1-7.0;
            lactic acid—1.48-4.9;
            propionic acid—1.48-3.36;
            butyric acid—0.74-1.68;
        in case of the second complex and the fourth mixture:
            twice-substituted sodium phosphate, 12-aqueous—33.0-36.48;
            sodium chloride—20.24-22.34;
            sodium acetate, 3-aqueous—4.0-4.43;
            potassium chloride—9.08-10.03;
            calcium chloride—8.85-9.77;
            magnesium sulphate—7.37-8.14;
            Na2EDTA or Na3DTPA—1.47-5.4;
            citric acid, anhydrous—2.95-4.56;
            lactic acid—1.4-4.56;
            propionic acid—1.4-3.13;
            butyric acid—0.71-1.56;

in case of the second complex and the fifth mixture:
  mono-substituted sodium phosphate, anhydrous—5.99-6.71;
  sodium chloride—30.82-34.5;
  sodium acetate, 3-aqueous—9.72-10.88;
  twice-substituted potassium phosphate, 3-aqueous—15.51-17.36;
  calcium chloride—9.99-11.18;
  magnesium sulphate—8.32-9.31;
  Na2EDTA or Na3DTPA—1.66-6.18;
  citric acid, anhydrous—3.33-5.22;
  lactic acid—1.6-5.22;
  propionic acid—1.6-3.58;
  butyric acid—0.8-1.79
in case of the second complex and the sixth mixture:
  twice-substituted sodium phosphate, anhydrous—16.85-19.09;
  sodium chloride—25.13-28.46;
  sodium acetate, 3-aqueous—4.98-5.64;
  potassium chloride—11.28-12.78;
  calcium chloride—10.99-12.45;
  magnesium sulphate—9.16-10.37;
  Na2EDTA or Na3DTPA—1.83-6.89;
  citric acid, anhydrous—3.66-5.81;
  lactic acid—1.76-5.81;
  propionic acid—1.76-3.98;
  butyric acid—0.88-1.99.

2. The acid-mineral composition of claim 1, wherein calcium chloride and magnesium sulphate are isolated from each other and from the other components of the acid-mineral composition.

3. An enteral solution for a lavage of a gastrointestinal tract and/or a correction of homeostasis disorders, comprising the acid-mineral composition of claim 1 and purified drinking water, said purified drinking water being present in an amount providing osmolarity of the enteral solution in a range from 280 to 310 mOsm/L and having a pH from 4.61 to 5.8.

* * * * *